US006586253B1

United States Patent
Harrison et al.

(10) Patent No.: US 6,586,253 B1
(45) Date of Patent: Jul. 1, 2003

(54) MICROCHIP BASED ENZYMATIC ANALYSIS

(75) Inventors: D. Jed Harrison, Edmonton (CA); Per E. Andersson, Stockholm (SE); Edgar Arriaga, Edmonton (CA); Gregor Ocvirk, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 09/058,702

(22) Filed: Apr. 10, 1998

(30) Foreign Application Priority Data

Feb. 27, 1998 (CA) ............................................. 2230653

(51) Int. Cl.[7] ............................................. G01N 33/543
(52) U.S. Cl. ............................ 435/514; 422/58; 422/63; 422/93; 422/98; 422/101; 435/7.4; 435/7.6; 435/287.1
(58) Field of Search ............................... 422/58, 63, 93, 422/98, 101; 435/7.4, 7.6, 287.1; 436/518, 514

(56) References Cited

U.S. PATENT DOCUMENTS

| | | | |
|---|---|---|---|
| 4,911,782 A | 3/1990 | Brown | 156/633 |
| 5,304,487 A | 4/1994 | Wilding et al. | 435/291 |
| 5,486,335 A | 1/1996 | Wilding et al. | 422/55 |
| 5,635,358 A | 6/1997 | Wilding et al. | 435/7.2 |
| 5,637,469 A | 6/1997 | Wilding et al. | 435/7.21 |
| 5,716,852 A | 2/1998 | Yager et al. | 436/172 |
| 5,726,026 A | 3/1998 | Wilding et al. | 435/7.21 |
| 5,726,751 A | 3/1998 | Altendorf et al. | 356/246 |

FOREIGN PATENT DOCUMENTS

| | | | |
|---|---|---|---|
| EP | WO93/22054 | 11/1993 | B01L/3/00 |
| EP | WO98/10267 | 3/1998 | G01N/15/14 |

OTHER PUBLICATIONS

Transport, Manipulation, and Reaction of Biological Cells On–Chip Using Electrokinetic Effects, Paul C.H. Li and D. Jed Harrison, Analytical Chemistry, Apr. 15, 1997, vol. 69, No. 8, p. 1564–1568. The abstract of this paper was published in Feb. 1997, more than one year before the filing of the instant application.

Capillary Electrophoresis and Sample Injection Systems Integrated on a Planar Glass Chip, D. Jed Harrison, A. Manz, Z. Fan, H. Lüdi, H.M. Widmer, Analytical Chemistry, 1992, vol. 64, p. 1926–1932.

Micromachining a Miniaturized Capillary Electrophoresis––Based Chemical Analysis System on a Chip, D.J. Harrison, K. Fluri, K. Seiler, Z. Fan, C.S. Effenhauser, A. Manz, Science, 1993, vol. 261, p. 895–897.

Micromachining of Capillary Electrophoresis Injectors and Separators on Glass Chips and Evaluation of Flow at Capillary Intersections, Z.H. Fan, D.J. Harrison, Analytical Chemistry, 1994, vol. 66, p. 177–184.

Electroosmotic Pumping and Valveless Control of Fluid Flow within a Manifold of Capillaries on a Glass Chip, K. Seiler, Z.H. Fan, K. Fluri, D.J. Harrison, Analytical Chemistry, 1994, vol. 66, p. 3485–3491.

Micromachining Chemical and Biochemical Analysis and Reaction Systems on Glass Substrates, D.J. Harrison, K. Fluri, N. Chiem, T. Tang, Z. Fan, Technical Digest, Transducers 95, 8th International Conference on Solid–State Sensors and Actuators, Stockholm, Jun. 25–29, 1995, p. 752–755.

Glass Chips for High–Speed Capillary Electrophoresis Separations with Submicrometer Plate Heights, C.S. Effenhauser, A. Manz, H.M. Widmer, Analytical Chemistry, 1993, vol. 65, p. 2637–2642.

Continuous Sample Preparation Using Free–Flow Electrophoresis on a Silicon Microstructure, D.E. Raymond, A. Manz, H.M. Widmer, Technical Digest, Transducers 95, 8th International Conference on Solid–State Sensors and Actuators, Stockholm, Jun. 25–29, 1995, p. 760.

Electrostatis Manipulation of Biological Objects in Microfabricated Structures, M. Washizu, in Integrated Micro–motion systems—Micromachining, Control and Applications, F. Harashima, Ed., Elsevier: New York, 1990, p. 417–431.

A Silicon Micromachined Device for Use in Blood Cell Deformability Studies, M.C. Tracey, R.S. Greenaway, A. Das, P.H. Kaye, A. Barnes, J. IEEE Trans. Biomed. Eng., 1995, vol. 42, p. 751–761.

Applications of a Microfabricated Device for Evaluating Sperm Function, L.J. Kricka, O. Nozaki, S. Heyner, W.T. Gorside, P. Wilding, Clin. Chem., 1993, vol. 39, p. 1944–1947.

High–Voltage Capillary Zone Electrophoresis of Red Blood Cells, A. Zhu, Y. Chen, J. Chromatogr. A, 1989, vol. 470, 251–260.

(List continued on next page.)

Primary Examiner—Bao-Thuy L. Nguyen
(74) Attorney, Agent, or Firm—Christensen O'Connor Johnson Kindness PLLC (57) ABSTRACT

A method for the detection of cell contents, the method comprising the steps of, introducing a cell into a channel in a microchip; lysing the cell to release cell contents into the channel; moving the cell contents towards a detection zone; and detecting the cell contents at the detection zone. An apparatus for the detection of cell contents, the apparatus comprising: a microchip; a cell mobilization channel formed in the microchip, the cell mobilization channel having a cell introduction end and a detection end; a cell mobilizer operably connected with the cell introduction end for moving cells from the cell introduction end to the detection end; means for lysing cells in the cell mobilization channel at a lysing zone, the lysing zone being located between the cell introduction end and the detection end; and a detector, disposed adjacent the detector end, arranged to detect cell contents appearing at the detector end that have been moved from the lysing zone to the detector end by the cell mobilizer.

24 Claims, 7 Drawing Sheets

OTHER PUBLICATIONS

Separation of hemoglobin variants in single human erythrocytes by capillary electrophoresis with lasser–induced native fluorescence detection, S.J. Lillard, E.S. Yeung, M.A. Lautamo, D.T. Mao, J. Chromatogr. A, 1995, vol. 718, p. 397–404.

Variability of Intracellular Lactate Dehydrogenase Isoenzymes in Single Human Erythrocytes, Q. Xue, E.S. Yeung, Analytical Chemistry, 1994, vol. 66, p. 1175–1178.

High–Speed Separation of Antisense Oligonucleotides on a Micromachined Capillary Electrophoresis Device, C.S. Effenhauser, A. Manz, H.M. Widmer, Analytical Chemistry, 1994, vol. 66, p. 2949–2953.

Ultra–high–speed DNA fragment separations using microfabricated capillary array electrophoresis chips, A.T. Woolley, R.A. Mathies, Proc. Nat. Acad. Sci., USA, 1994, vol. 91, p. 11348–11352.

Novel bispecific immunoprobe for rapid and sensitive detetion of prostate–specific angtigen, F.T. Kreutz, M.R. Suresh, Clin. Chem., 1997, vol. 43, p. 649–656.

Normal Serum β–Galactosidase in Juvenile GM1 Gangliosiddosis, N. Ishii, A. Oshima, H. Sakuraba, Y. Fukuyama, Y. Suzuki, Ped. Neurol., 1994, vol. 10, p. 317–319.

The Fucosyltransferase FucT–VII Regulates E–Selectin Ligand Synthesis in Human T Cells, R.N. Knibbs et al., J. Cell Biol., 1996, vol. 133, p. 911–919.

Efficient transfer of genetic material into mammalian cells using Starburst polyamidoamine dendrimers, J.F. Kukowska–Latallo et al., Proc. Nat. Acad. Sci., USA, 1996, vol. 93, p. 4897–4902.

Biological Cell Assays on an Electrokinetic Microchip, P.E. Andersson, P.C.H. Li, R. Smith, R.J. Szarka, D.J. Harrison, Technical Digest: 1997 International Conference on Solid–State Sensors and Actuators, Transducers 97, Jun. 16–19, 1997, p. 1311–1314.

Integrated Capillary Electrophoresis Devices with an Efficient Postcolumn Reactor in Planar Quartz and Glass Chips, Fluri et al., Analytical Chemistry, 1996, vol. 68, p. 4285–4290.

Manipulation of a single cell with microcapillary tubing based on its electrophoretic mobility, Kitagawa et al., Electrophoresis, 1995, vol. 16, p. 1364–1368.

Micromachining: A new direction for clinical analyzers, Kricka et al., Pure and Applied Chemistry, 1996, vol. 68, p. 1831–1836.

Stacked modules for micro flow systems in chemical analysis: concept and studies using an enlarged model, Fettinger et al., Sens. Actuat. B. 17, 1993, p. 19–25.

Normal Cations and Abnormal Membrane Lipids in the Red Blood Cells of Dogs with Familial Stomatocytosis–Hypertrophic Gastritis, Slappendel et al., J.J. Blood, 1994, vol. 84, p. 904–909.

Planar Glass Chips for Capillary Electrophoresis: Repetitive Sample Injection, Quantitation, and Separation Efficiency, Seiler et al., Analytical Chemistry, 1993, vol. 65, p. 1481–1488.

Introduction of a yeast artificial chromosome vector into *Saccharomyces cerevisiae* cells by electroporation, Rech et al., Nucleic Acids Res., 1990, vol. 18, p. 1313.

Electrical Breakdown of Bimolecular Lipid Membranes as an Electromechanical Instability, J.M. Crowley, Biophys. J., 1973, vol. 13, p. 711–724.

Dielectric Breakdown of Cell Membranes, Zimmermann et al., Biophys. J., 1974, vol. 14, p. 881–889.

Reversible and irreversible modification of erythrocyte membrane permeability by electric field, Serpersu et al., Biochim., Biophys., Acta., 1985, p. 812, 779.

High efficiency transformation of *E.coli* by high voltage electroporation, Dower et al., Nucleic Acids Res., 1988, vol. 16, p. 6127–6145.

Martin U. Kopp et al., *Chemical Amplification: Continuous–Flow PCR On A Chip*, Science Magazine, vol. 28, pp. 1046–1048, May 15, 1998.

Peter Wilding et al., *Manipulation and Flow of Biological Fluids in Straight Channels Micromachined in Silicon*, Clinical Chemistry, vol. 40, No. 1, 1994, pp. 43–47.

1. INTRODUCTION OF A SINGLE CELL
2. LYSIS
3. INCUBATION WITH SUBSTRATE
4. DETECTION OF PRODUCT(S)

PREINCUBATED HL 60 CELLS
(1.6*10$^6$ CELLS/mL); IN PBS/5% FCS

LASER: 3.7 mW; PMT: 850V; PINHOLE: 600 μM FLOW VELOCITY

LASER: 3.7 mW; PMT: 850V; PINHOLE: 600 µM FLOW VELOCITY

MICROCHIP BASED ENZYMATIC ANALYSIS

FIELD OF THE INVENTION

This invention relates to cell assays on microchips.

BACKGROUND OF THE INVENTION

Several methods are known for enzymatic assays, such as use of flow cytometry, fluorescence microscopy, and capillary electrophoresis, and a great deal of work is being done on these systems to improve system performance characteristics such as average activity, distribution, separation of products, sensitivity, throughput, analysis time and quantitation. Due to the very small quantities involved, and the desire to detect small concentrations of products, improvement of all of the system performance characteristics, without degradation of any, is very difficult. There is thus a need for a device system showing improvement in all of these system performance characteristics.

One particular enzyme for which detection of small quantities is important is β-galactosidase. Deficiency in β-galactosidase is symptomatic of diseases such as GM1-gangliosidosis, galactosialidosis and Morquio B syndrom (mucopolysaccharidosis (MPS) IV B). These are genetic diseases that onset at various ages, and affect a variety of cell types, including brain tissue, leukocytes and skin fibroblasts. β-galactosidase is also used as a product of a reporter gene in recombinant DNA work. Enzymatic assays are available in which suspended cell populations from a patient are analyzed using flow cytometry. While this is a single cell method, the technique reports the results from an ensemble of cells measured at one point in time.

SUMMARY OF THE INVENTION

This invention relates to a microchip system in which products from lysed cells are detected. A microchip format allows for detailed evaluation of the kinetics of response of each cell in an enzymatic assay. This makes it is easier to sort cell responses into different categories. In flow cytometry the cells remain intact and the substrate must cross the cell membrane. The limited amount which transports across, and the low rate at which this occurs means that cells must be incubated for hours before analysis. Performing the β-galactosidase assay within a microchip allows for a novel sequnce of analysis that substantially speeds up the assay over flow cytometry methods.

There is therefore provided in accordance with an aspect of the invention, a method for the detection of cell contents, the method comprising the steps of introducing a cell into a channel in a microchip; lysing the cell to release cell contents into the channel; moving the cell contents towards a detection zone; and detecting the cell contents at the detection zone.

In accordance with a further aspect of the invention, there is provided an apparatus for the detection of cell contents, the apparatus comprising: a microchip; a cell mobilization channel formed in the microchip, the cell mobilization channel having a cell introduction end and a detection end; a cell mobilizer operably connected with the cell introduction end for moving cells from the cell introduction end to the detection end; means for lysing cells in the cell mobilization channel at a lysing zone, the lysing zone being located between the cell introduction end and the detection end; and a detector, disposed adjacent the detector end, arranged to detect cell contents appearing at the detector end that have been moved from the lysing zone to the detector end by the cell mobilizer.

In further aspects of the invention, the cells are mammalian cells and the cell contents comprise β-galactosidase. The cell contents may be moved towards the detection zone by electrophoretic, electroosmotic forces, pumping, or other mobilization methods. The cell may be lysed by various techniques such as application of an electric field across the cell, or by introduction of a reagent into the channel. The channel dimensions should be similar to the cell dimensions, preferably not more than about twelve cell diameters.

These and other aspects of the invention are described in the detailed description of the invention and claimed in the claims that follow.

BRIEF DESCRIPTION OF THE DRAWINGS

There will now be described preferred embodiments of the invention, with reference to the drawings, by way of illustration only and not with the intention of limiting the scope of the invention, in which like numerals denote like elements and in which.

DETAILED DESCRIPTION OF PREFERRED EMBODIMENTS

Figure 1:
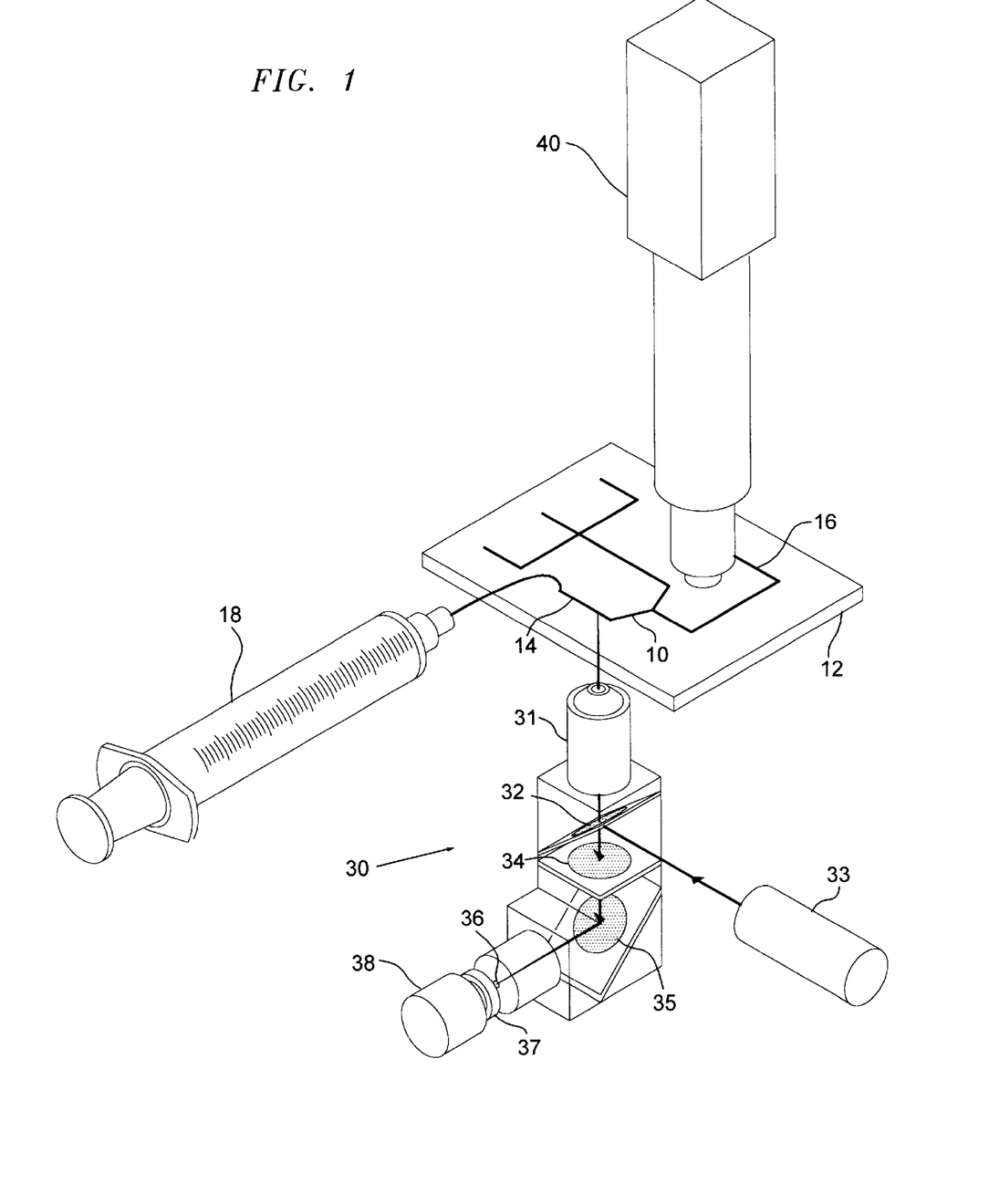
FIG. 1 is a schematic isometric view of a microchip based enzymatic analysis system according to the invention.

Referring to FIG. 1, there is shown apparatus for the detection of cell contents. A cell mobilization channel 10 is formed in a microchip 12 by any of a number of conventional methods. The microchip 12 may be made of glass, silica or other materials that may be micromachined to produce channels that have dimensions of from 10 μm to 100 μm cross-sectional dimensions. In a microchip, the channels are formed between two plates, at least one of which has the channel formed in it. The other plate normally acts as a lid. Fabrication techniques for microchips are well known and need not be described here. The cell mobilization channel 10 should have a minimum cross-section that is at least larger than the cells to be assayed by an amount sufficient to prevent blocking of the channel with the cells and a maximum cross-section that is smaller than about twelve times the diameter of the cells to be assayed, such that the cells do not interfere with each other to such an extent that the detection signal is degraded. The channel 10 has a cell introduction end 14 and a detection end 16. A syringe or micropump 18, functioning as a cell mobilizer operably connected with the cell introduction end 14, communicates as for example by a flexible capillary 20 with the cell introduction end 14. The introduction of cells into the channel 10 is carried out according to conventional methods and need not be described further. Although a syringe 18 is shown as the cell mobilizer, other devices may be used such as a vacuum pump, DC electroosmosis systems, electrophoretic systems or dielectrophoresis systems, particularly where biochemical separations are incorporated in the system. When using electrical systems to move the cells, in which electrodes are contacted with solution in the channel at opposed ends of the channel, care must be taken that the voltages are not so high so as to cause unintentional lysis.

Figure 2:
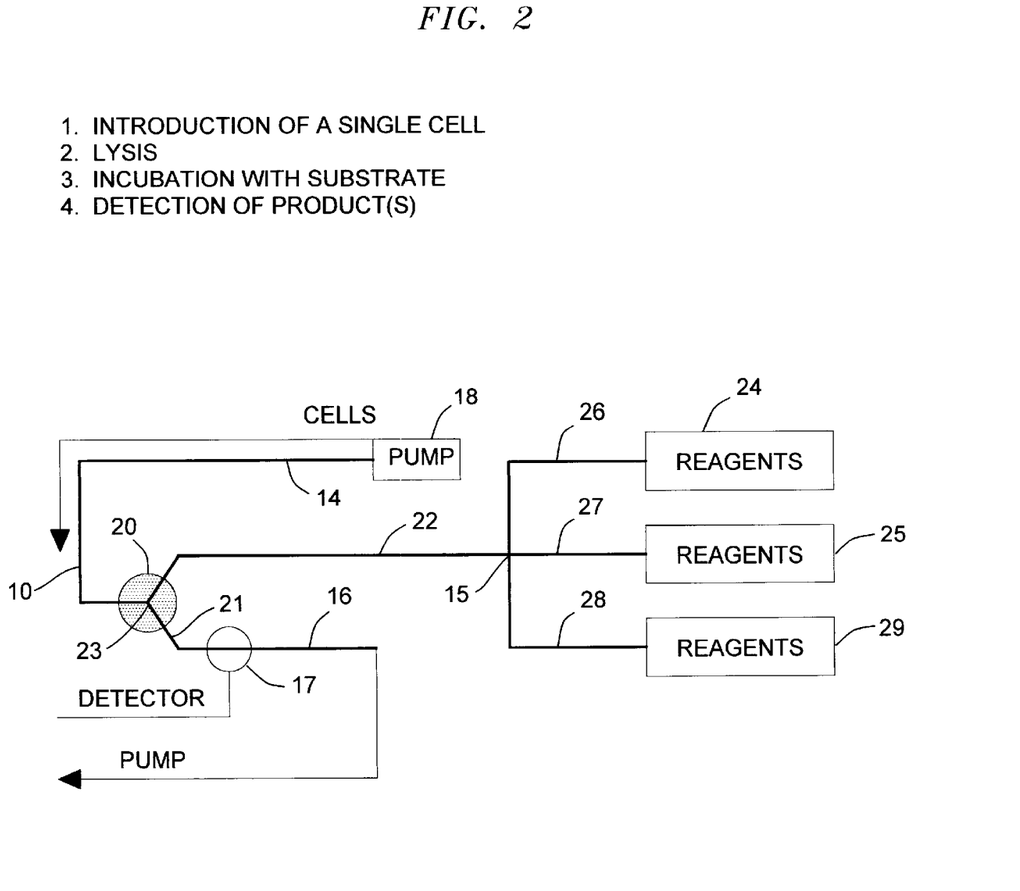
FIG. 2 is a plan view of the microchip of FIG. 1.

Means are provided for lysing cells in a lysing zone 20 located between the cell introduction end 14 and the detector end 16. Various means may be used to lyse the cells. As shown in FIGS. 1 and 2, the lysing means may comprise a microchannel 22 intersecting with the channel 10 at the lysing zone 20 and a reagent source 24 communicating with the microchannel 22 through a channel 26. Another method of lysing the cells is to apply a strong electric field (eg 3–10 kV/cm, although this may depend on the cells) across the cells, with sufficient gradient to destroy the cell wall. Electrodes contacting the channel 10 at its opposed ends may be used to accomplish this. Alternatively, an electric field may be applied across channel 10 through two channels that intersect with channel 10, similar to the manner in which channels 26 and 28 intersect with the channel formed by channels 22 and 27. All of the channels 22, 26 etc described herein are formed by conventional microchip manufacturing methods such as etching or laser ablation. Enzyme substrate may be introduced with the lysing agent, or separate from the lysing agent, for example in a channel intersecting the channel 10 at a location upstream or downstream of the lysing zone 20.

A detector 30 is disposed adjacent the detector end 16 and is arranged to detect cell contents appearing at the detector end 16 that have been moved from the lysing zone 20 to the detector end 16 by the cell mobilizer 18. In the example shown, the detector 30 comprises a 40×0.6 N.A. microscope objective 31 focussed on the detection zone 17 in the detection end 16, a dichroic mirror 32 arranged in the path of light from the objective 31 and disposed to mix light from an argon ion laser 33 with the light from the objective to form a beam which passes through a 200 mm tube lens 34, thence to a mirror 35, through a pinhole 36, bandpass filter 37 to photomultiplier tube 38. Included with the detector 30 in the example is an imaging camera and microscope 40 to allow observation of the flowing cell stream or the fluorescing product. Performing an enzymatic assay with a microchip allows for a novel sequence of analysis that substantially speeds up the assay over flow cytometry methods.

To operate the system, cells are introduced into the channel 10 in chip 12 by pump 18 and mobilized towards the lysing zone 20. At the lysing zone 20 the cells are met with a lysing agent that has been introduced into the lysing zone 20 through channels 22 and 26 by reagent source 24. Action of the lysing agent on the cells frees the cell contents, including target enzymes, to react with a solution phase substrate which may be contained in the lysing medium, or introduced from another flow channel downstream of the lysing zone 20.

Cells are transported through the chip 12 and isolated individually in the lysing zone 20, lysed, then reacted with substrate. The detector zone 17 and lysing zone 20 should be sufficiently distant from each other that separation of material within the channel 10 occurs, in order to reduce background from other material within the channel 10 and scattering from the lysed cell debris. Cells may also be introduced into the lysing zone 20 in the following manner. Cells may be pumped from channel 26 to channel 28 across intersection 15. The flow is stopped with some cells at the intersection. Then, a voltage is applied between for example the end of channel 27 and the end of channel 16 to cause the cells to move towards the detection zone 20. In this situation, the cell introduction channel is channel 22 and channel 10 is not required.

Several improvements result from this type of procedure for the detection of for example enzymes. The intracellular fluid is often at a pH below the optimum for enzyme activity or optimal fluorescence yield. Lysing the cell in an appropriate buffer, say phosphate at pH 7.4, releases enzyme into a more suitable environment for reaction with the enzyme, increasing the amount of product produced per unit time. Ingress of the substrate into a cell can vary with the age and condition of a cell, introducing considerable variability into quantitation of the amount of enzyme present, because the amount of substrate in side the cell varies. Releasing the enzyme into a uniform background of substrate within a flow channel reduces this problem. By working in a chip 12 with well defined flow channels 10, with a cross sectional area similar to that of a cell, the dilution of the enzyme is minimized, so the signals will remain large.

Figure 3:
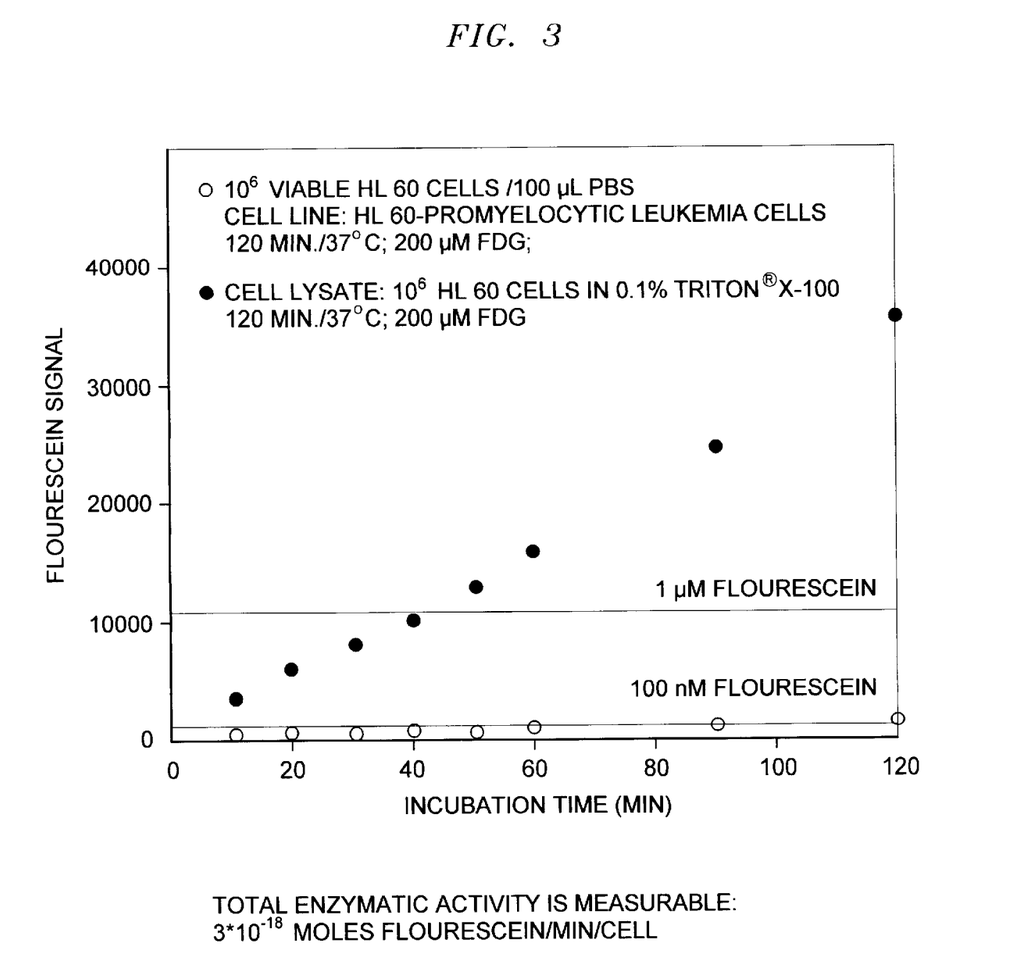
FIG. 3 is a graph showing results of lysing of single cells and identification of β-galactosidase on a microtitre plate.

FIG. 3 shows the results of an analysis of HL60 cells (immortalized human cell line) performed by microtitre plate assay. The signal developed by intact cells increases with time, but the signal for lysed cells grows much faster. This result confirms that the product yield from the enzyme assay is much faster when the cells are first lysed. The results also show that the HL60 cell, when lysed, generates product at the rate of $3\times10^{-18}$ moles/min./cell. This rate is high enough that the fluorescent product of a single cell can be expected to be detected on a chip after a few seconds to a few minutes reaction time.

Figure 4:
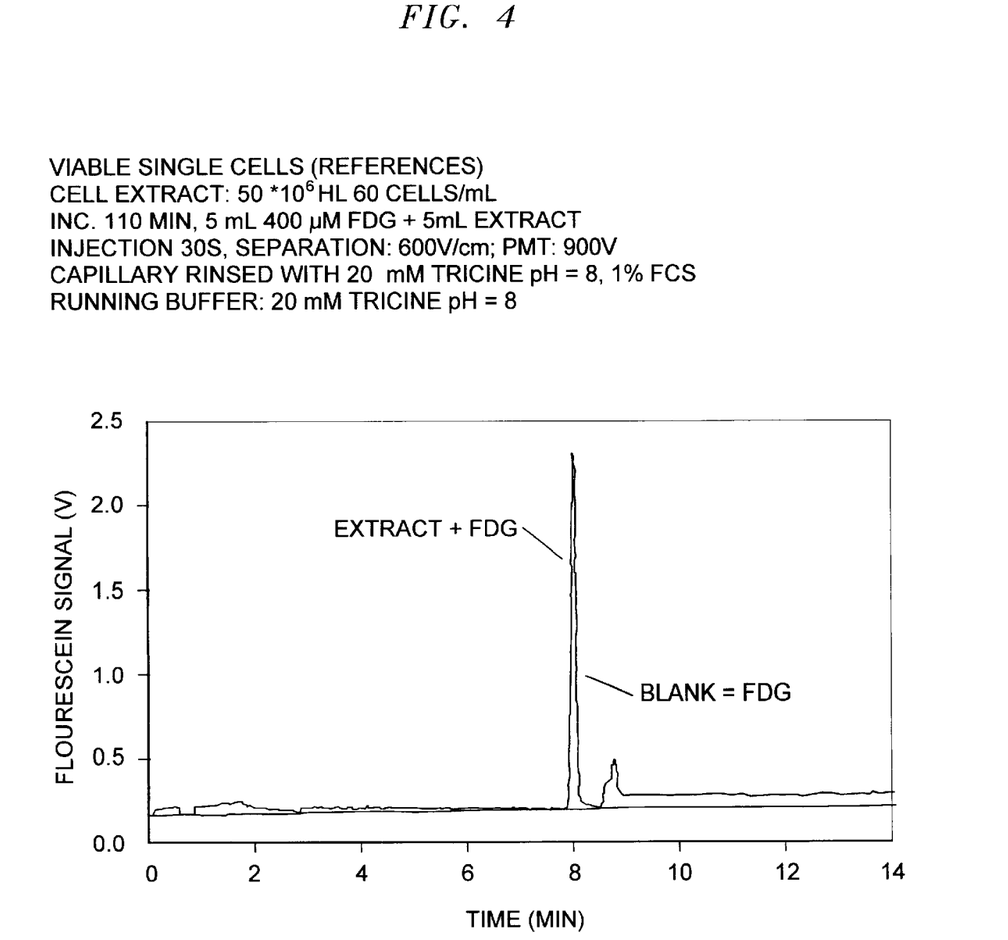
FIG. 4 shows identification of single cells using capillary electrophoresis.

FIG. 4 illustrates the results of an analysis of a cell lysate within a capillary, in which the cells were first lysed, reacted with substrate and a small volume was introduced into the capillary. The high quality peak formed was achieved by the addition of 5%, deactivated fetal calf serum (FCS) to the buffer solution (20 mM tricine pH 8). Blank solutions gave much smaller peaks for the fluorescent product, indicating the FCS treatment was able to reduce carryover of enzyme from run to run. In this example the ratio of enzyme to substrate favoured formation of FMG, but other ratios produce fluorescein or a mixture of both products.

A demonstration of cell lysis followed by analysis of the β-galactosidase content was performed in the device illustrated in FIGS. 1 and 2. A syringe pump 18 or a vacuum source provided negative pressure on the analysis channel 10. Cells were introduced upstream of a y-shaped mixer (at the lysing zone 20) and were mixed with reagents that were premixed upstream along long channel 22. A manifold of channels 26, 27, 28 provided the means to deliver and mix a variety of reagents at will from reagent sources 24, 25 and 29. Cells were mixed with the reagents at the y-intersection (lysing zone 20), and consequently lysed by a chemical lysing agent such as sodium dodecylsulfate.(SDS), Triton X-100, $Cu^{2+}$ or other agents. Charged surfactants such as SDS will tend to deactivate the cellular enzymes, while neutral surfactants such as Triton X-100 will not. The enzyme substrate was then transformed by the enzyme into a detectable product, such as a fluorescent or optically absorbing product, or an electrochemically active product. An example of a fluorescence detection apparatus that could be used with the chip is illustrated in FIG. 1

Figure 5A:
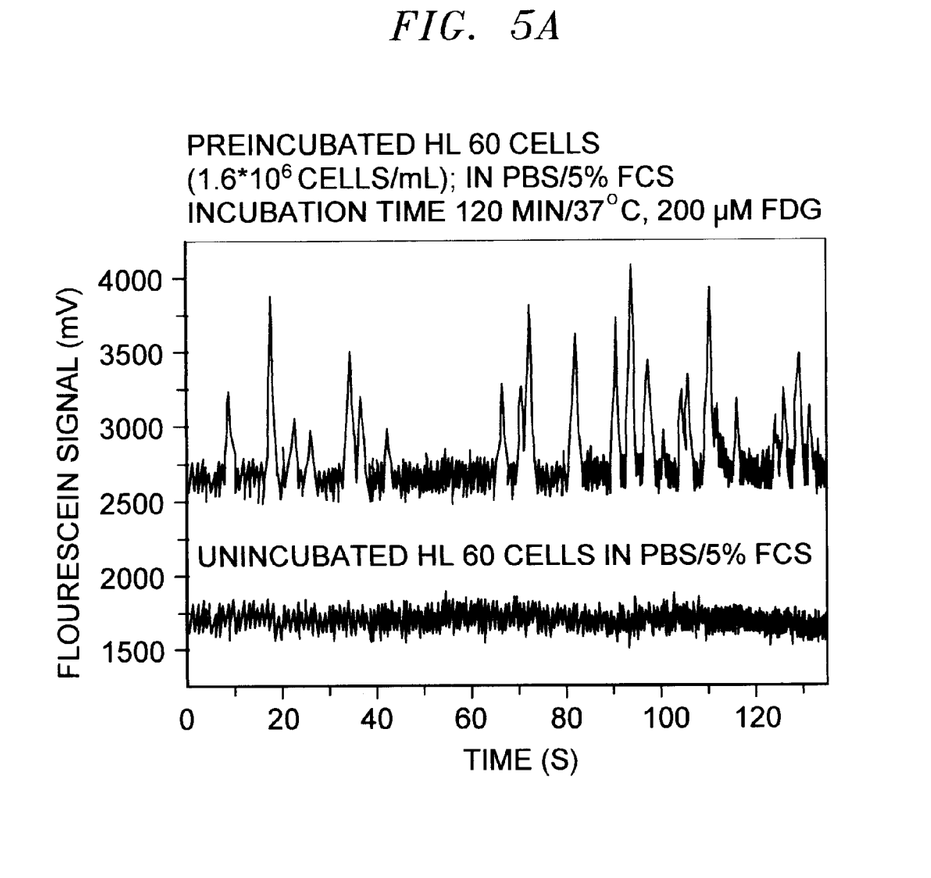
FIGS. 5A and 5B show cell content identification results obtained for HL60 cells pre-incubated with the substrate FDG at 200 μM in phosphate buffered saline (PBS) with 5% FCS, using the channel configurations illustrated in FIGS. 5C and 5D respectively.
Figure 5B:
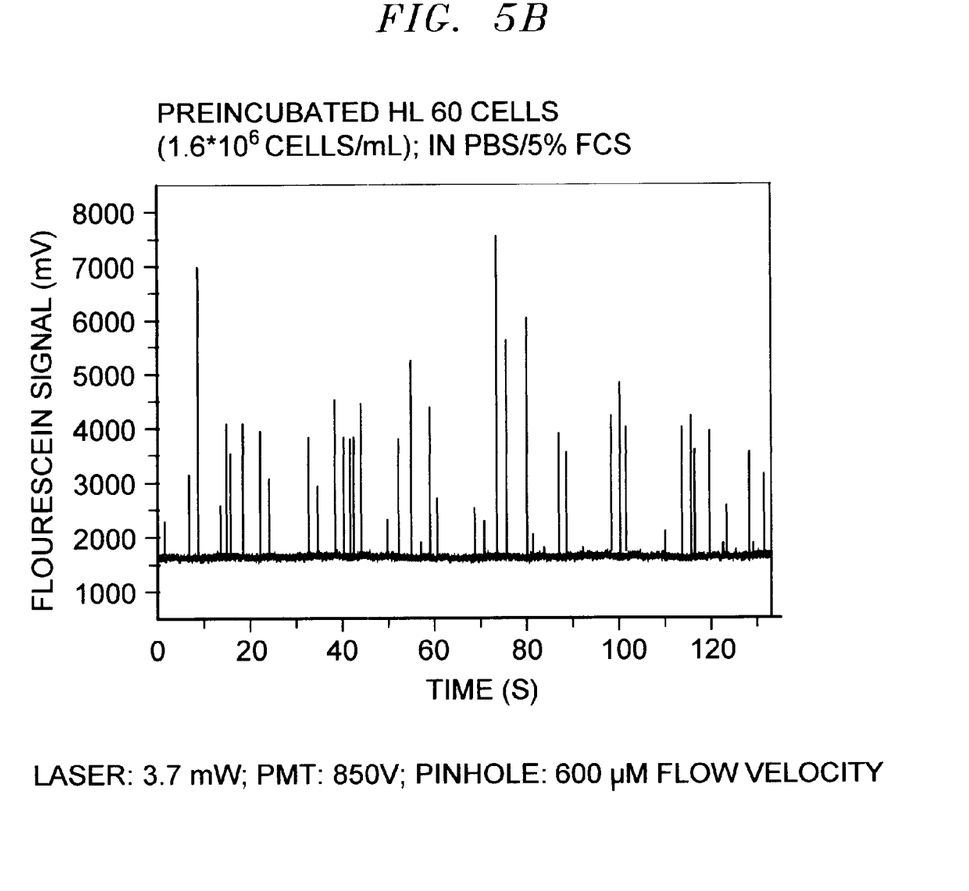
Figure 5C:
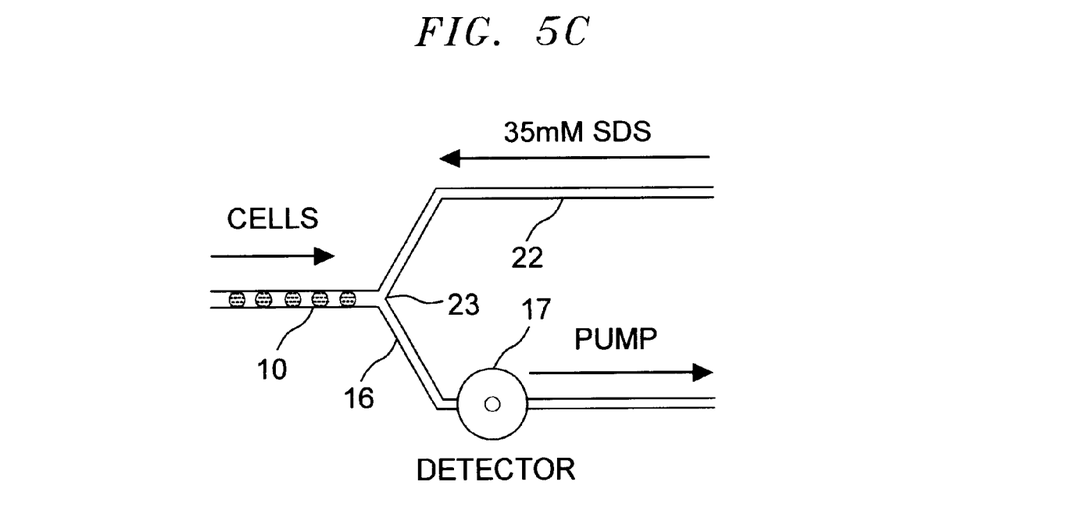
Figure 5D:
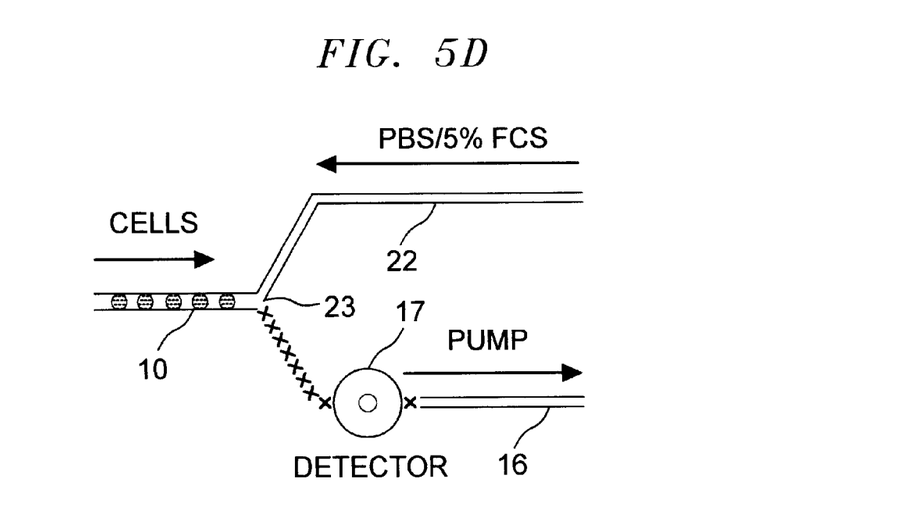

FIG. 5A shows results obtained for HL60 cells pre-incubated with the substrate FDG at 200 $\mu$M in phosphate buffered saline (PBS) with 5% FCS. The cells were then introduced into the chip 12 and mobilized towards the reaction zone 20 at the y-intersection 23 with a negative pressure on the detector channel 16. A solution of 35 mM SDS was mixed with the cells to cause lysis. This reagent rapidly lyses the cells, but it also significantly deactivates the enzyme, so the signal seen was generated by the release of product formed within the cells during the pre-incubation period. Control experiments are shown in FIG. 5B. Cells that were not incubated with FDG show no signal when introduced into the chip. Cells incubated with FDG but which do not mix with SDS before reaching the detector show very sharply spiking signals, that do not have the peak width consistent with diffusion of enzyme after release from the cells, and so correspond to light scattering events. The control experiments verify that the peaks are due to substrate reaction with substrate and not from light scattering or from other components within the cells.

Figure 6A:
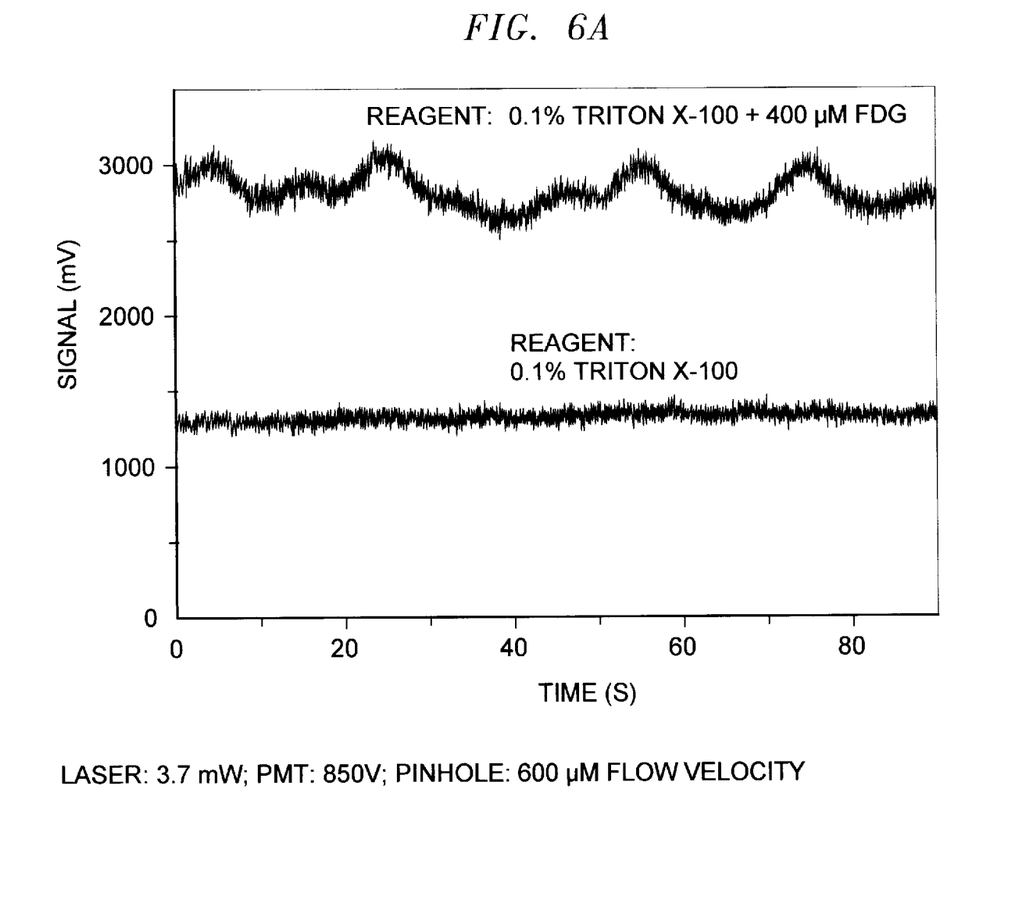
FIG. 6A shows cell content identification results obtained for HL60 cells that were not pre-incubated with FDG using the channel configuration illustrated in FIG. 6B.
Figure 6B:
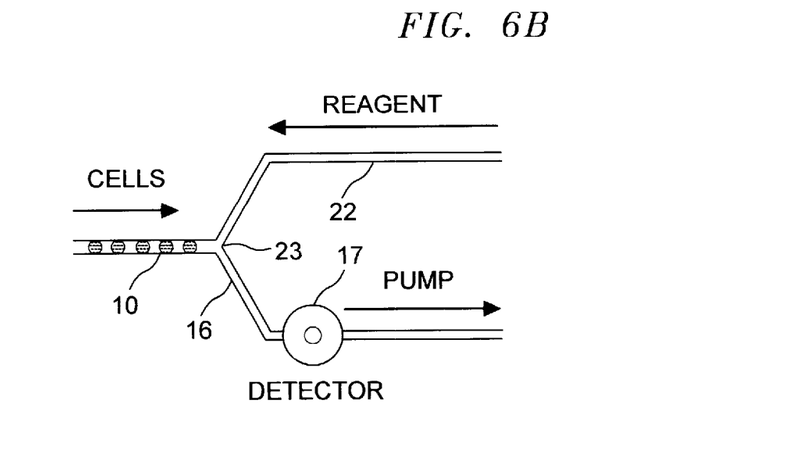

FIG. 6A shows results obtained for HL60 cells that were not pre-incubated with FDG. Instead the HL60 cells introduced to channel 10 are mixed at the y-intersection 23 with a reagent stream through channel 22 containing the lysing agent Triton X-100 and 400 μM FDG and the resulting product formed is measured downstream in the channel 16 at the detection zone 17. The control experiment here shows that when the FDG is omitted from the lysing reagent stream no signal is observed. This confirms that the peaks seen are not due to scattering and arise from the presence of the dye. The Triton X-100 lyses cells more slowly than does SDS so it was necessary to ensure about 1 min. elapsed between the time of mixing and the detection point, by controlling the flow rate or varying the position of the detector. Other neutral surfactants such as Tween 20 or Brij 35 could be used to induce cell lysis without inhibiting enzyme activity.

Identical experiments to those shown in FIGS. 5A and 5B were performed with human lymphocytes, yielding qualitatively similar results, indicating the analysis method can be used with cells derived from human blood samples.

Electric fields used with or without additional chemical lysing agent can also be used to lyse the cells. Application of electric fields of 50 V/cm or greater to the flow channels lyses lymphocytes and leukocytes on-chip. This effect can be used to release the cellular enzymes. It may be used to enhance the lysing rate of agents such as Triton X-100 or Tween 20.

Transport can be effected by the use of electric fields instead of pumps. However the electric field must be low enough (less than say 50 V/cm) to avoid cell lysis before the intended point. Electric fields are applied with electrodes inserted into fluid reservoirs at the ends of the channels. Different potentials applied on each channel are used to control the relative flow rate from each channel. The same electrodes are then used to apply higher fields to lyse the cells and to effect separation of the reaction products from each other and from any cell debris that may affect the reaction.

Various cells may be used in the system, besides mammalian cells such as yeast and *E.coli*. For mammalian cells such as canine erythrocytes (blood cells), eletroosmosis pumping may be used, with chemical lysis by application of sodium dodecylsulfate (SDS) through a channel such as channel 22.

The chip 12 may also be used for cell-based drug screening. The walls of the channel 10 may be coated with a suitable coating to prevent the adsorption of cells, such as a coating with 5% Fetal calf serum in 1640 RPMI solution to prevent adsorption in the case of lymphocytes and leukocytes.

A stream of cells may be provided from one channel 10 and mixed with an inhibitor from another (lysing zone). The incubation time can be controlled by the flow velocity. The cells may then be brought into contact with an activator at a later junction 21, flow stopped, upon which the activator diffuses to meet the cell (0.25 s is required for the 30 μm wide channel) and initiates a change. If the cell contains a stain that signals the change, the event can be recorded with a video or still camera. This approach provides accurate kinetic data at the level of an individual cell, with well controlled, multiple deliveries of reagent at different locations within the device. The device provides a means to screen candidate drugs which can inhibit the activator's function. Such systems have much greater versatility and better kinetic resolution for the study of single cell events than does flow cytometry.

Many other intracellular enzymes can also be evaluated using these devices. For example, the enzyme Fucosyltransferase can be analyzed using a fluorogenically labelled olligosacharide substrate which is cleaved in the presence of the enzyme, generating a fluorescent signal. In addition, luciferase may also be analyzed. Reporter genes that are incorporated into cells using recombinant DNA techniques are designed to produce enzymes such as b-galactosidase or proteins such as aeuquorin. These cell assay devices can be used to determine the succesful transfection and expression of such reporter genes.

A person skilled in the art could make immaterial modifications to the invention described in this patent document without departing from the essence of the invention that is intended to be covered by the scope of the claims that follow.

The embodiments of the invention in which an exclusive property or privilege is claimed are defined as follows:

1. A method for the detection of cell contents, the method comprising the steps of:
   introducing a stream of multiple cells into a channel in a microchip;
   individually isolating a cell from the stream of multiple cells in a lysing zone and lysing the cell in the lysing zone to release enzymes into the channel;
   reacting the enzymes with a substrate to yield a reaction product;
   moving the reaction product towards a detection zone; and
   detecting the reaction product at the detection zone.

2. The method of claim 1 in which the enzymes are selected from the group consisting of luciferase, β-galactosidase and Fucosyltransferase.

3. The method of claim 1 in which the enzymes are produced by reporter genes that have been transfected into the cell.

4. The method of claim 1 in which the cell is lysed by application of an electric field across the cell.

5. The method of claim 1 in which the cell is lysed by introduction of a reagent into the channel.

6. The method of claim 1 in which lysing of the cell is carried out by application of an electric field across the cell assisted by introduction of a reagent.

7. The method of claim 1 in which the channel dimensions are not more than twelve times the cell diameter.

8. The method of claim 1 in which enzyme substrate is introduced into the channel at a location downstream from the introduction of the lysing agent.

9. A method for the detection of cell contents, the method comprising the steps of:
   introducing a stream of multiple cells into a channel in a microchip;

individually isolating a cell from the stream of multiple cells in a lysing zone and lysing the cell by application of an electric field across the cell in the lysing zone to release cell contents into the channel;

moving the cell contents towards a detection zone; and detecting the cell contents at the detection zone.

10. The method of claim 9 in which the cell is a mammalian cell and the cell contents comprise enzymes.

11. The method of claim 10 in which the enzymes are selected from the group consisting of luciferase, β-galactosidase and Fucosyltransferase.

12. The method of claim 9 in which the enzymes are produced by reporter genes that have been transfected into the cell.

13. The method of claim 9 in which lysing of the cell is carried out by application of an electric field across the cell assisted by introduction of a reagent.

14. The method of claim 9 in which the channel dimensions are not more than twelve times the cell diameter.

15. The method of claim 9 in which, after introducing the cell into a channel, the cell is moved to a lysing zone at an intersection of the channel and a cross-channel, the cell is stopped at the lysing zone and the cell is lysed by application of an electric field applied along the cross-channel.

16. A method for the detection of cell contents, the method comprising the steps of:

introducing a stream of multiple cells into a channel in a microchip;

individually isolating a cell from the stream of multiple cells in a lysing zone and lysing the cell to release cell contents into the channel at the lysing zone;

reacting the cell contents with a substrate at a reaction zone downstream of the lysing zone to yield a reaction product;

moving the reaction product towards a detection zone; and detecting the reaction product at the detection zone.

17. The method of claim 16 in which the cell is a mammalian cell and the cell contents comprise enzymes.

18. The method of claim 17 in which the enzymes are selected from the group consisting of luciferase, β-galactosidase and Fucosyltransferase.

19. The method of claim 16 in which the enzymes are produced by reporter genes that have been transfected into the cell.

20. The method of claim 16 in which the cell is lysed by application of an electric field across the cell.

21. The method of claim 16 in which the cell is lysed by introduction of a reagent into the channel.

22. The method of claim 16 in which lysing of the cell is carried out by application of an electric field across the cell assisted by introduction of a reagent.

23. The method of claim 16 in which the channel dimensions are not more than twelve times the cell diameter.

24. A method for the detection of cell contents, the method comprising the steps of:

introducing a stream of multiple cells into a channel in a microchip;

individually isolating a cell from the stream of multiple cells in a lysing zone and lysing the cell by application of an electric field across the cell in the lysing zone to release cell contents into the channel;

reacting the cell contents with a substrate to create reaction products;

moving the reaction products towards a detection zone; and detecting the reaction products at the detection zone.

* * * * *

UNITED STATES PATENT AND TRADEMARK OFFICE
CERTIFICATE OF CORRECTION

PATENT NO. : 6,586,253 B1
DATED : July 1, 2003
INVENTOR(S) : D.J. Harrison et al.

It is certified that error appears in the above-identified patent and that said Letters Patent is hereby corrected as shown below:

Title page,
Item [56], References Cited, OTHER PUBLICATIONS, insert in appropriate order:
-- Microfluidic System and Methods of Use, Daniel Jed
Harrison, Per Andersson, Paul Li, Roderick Szarka,
and Richard Smith, May 16, 1997, U.S. application sn.
08/858,087, and also provisional application sn.
60/047,024 filed May 19, 1997. --

Signed and Sealed this

Twentieth Day of January, 2004

JON W. DUDAS
*Acting Director of the United States Patent and Trademark Office*